United States Patent [19]

Lele

[11] Patent Number: 4,938,217

[45] Date of Patent: Jul. 3, 1990

[54] ELECTRONICALLY-CONTROLLED VARIABLE FOCUS ULTRASOUND HYPERTHERMIA SYSTEM

[75] Inventor: Padmakar P. Lele, Winchester, Mass.

[73] Assignee: Massachusetts Institute of Technology, Cambridge, Mass.

[21] Appl. No.: 209,517

[22] Filed: Jun. 21, 1988

[51] Int. Cl.$^5$ .............................................. A61N 5/00
[52] U.S. Cl. .................................. 128/399; 128/24 A; 73/618
[58] Field of Search ................ 128/24 A, 399, 660.03, 128/660.09; 73/618

[56] References Cited

U.S. PATENT DOCUMENTS

| | | | |
|---|---|---|---|
| 4,397,314 | 8/1983 | Vaguine | 128/399 |
| 4,441,486 | 4/1984 | Pounds | 128/24 A |
| 4,549,533 | 10/1985 | Cain et al. | 128/24 A |
| 4,556,070 | 12/1985 | Vaguine et al. | 128/804 |
| 4,586,512 | 5/1986 | Do-huu et al. | 128/660 |
| 4,620,546 | 11/1986 | Aida et al. | 128/660 |
| 4,622,972 | 11/1986 | Giebeler, Jr. | 128/399 |
| 4,646,756 | 3/1987 | Watmough et al. | 128/804 |
| 4,658,828 | 4/1987 | Dory | 128/399 X |
| 4,708,127 | 11/1987 | Abdelghani | 128/24 A |
| 4,757,820 | 7/1988 | Itoh | 128/660.03 |

FOREIGN PATENT DOCUMENTS 0214782  3/1987  European Pat. Off. .

OTHER PUBLICATIONS

Lele, P. P., 1975, "Hyperthermia by Ultrasound", Proceedings of the International Symposium on Cancer Therapy by Hyperthermia and Radiation, American College of Radiology, Washington, D.C., pp. 168-178.
Lele, P. P., 1981, "An Annular-Focus Ultrasonic Lens for Production of Uniform Hyperthermia in Cancer Therapy", Ultrasound in Medicine and Biology, pp. 191-193.
Lele, P. P., 1983, "Physical Aspects and Clinical Studies with Ultrasonic Hyperthermia", Hyperthermia in Cancer Therapy, G. K. Hall and Co., pp. 333-367.
Sleefe, G. E. and Lele, P. P., 1985, "Phased Arrays for the Induction of Local Hyperthermia", Proceedings of the IEEE 1985 Ultrasonics Symposium.
Lele, P. P., 1987, "Ultrasound: Synergistic Effects and Application in Cancer Therapy by Hyperthermia", Ultrasound, Plenum Publishing Corporation, pp. 307-332.
Lele, P. P., 1987, "Effects of Ultrasound on 'Solid' Mamalian Tissues and Tumors in Vivo", Ultrasound, Plenum Publishing Corporation, pp. 275-306.
Lele, P. P., 1986, "Rationale, Technique and Clinical Results with Scanned, Focused Ultrasound (SIMFU) System", IEEE Eigth Annual Conferenece of the Engineering in Medicine and Biology Society.

Primary Examiner—Lee S. Cohen
Attorney, Agent, or Firm—Thomas J. Engellenner; David A. Jacobs

[57] ABSTRACT

A therapeutic ultrasound hyperthermia system utilizes a phased array of ultrasound transducer elements. By varying the phase delays in the excitation of individual transducer elements, the focal depth of the ultrasonic beam can be varied, without changing the distance between the transducer and the patient. The phased array of transducer elements can be an array of rectangular elements which are rotated about an axis to deliver ultrasound to the target region while minimizing overall heating effect in the treatment areas outside the target region.

8 Claims, 3 Drawing Sheets

ELECTRONICALLY-CONTROLLED VARIABLE FOCUS ULTRASOUND HYPERTHERMIA SYSTEM

The U.S. Government has rights in this invention pursuant to Contract No. CA 31303-03 awarded by the National Cancer Institute.

BACKGROUND OF INVENTION

This invention relates generally to systems for ultrasound hyperthermia, and, more particularly, relates to apparatus and methods for delivering ultrasonic energy in hyperthermic treatment of internal cancers and other diseases which respond to temperature elevation.

Production of a controllable level of temperature elevation or hyperthermia at pre-selected locations and volumes of tissue has been found to be of significant therapeutic value in the treatment of patients with cancer or other diseases. Several methods utilizing focused ultrasound to produce such hyperthermia have been described in the art. See, for example, the following publications:

Lele, P. P., 1975, "Hyperthermia by Ultrasound," Proceedings of the International Symposium on Cancer Therapy by Hyperthermia and Radiation, American College of Radiology, Washington, D.C., pp. 168–178;

Lele, P. P., 1981, "An Annular-Focus Ultrasonic Lens for Production of Uniform Hyperthermia in Cancer Therapy", Ultrasound in Medicine and Biology, pp. 191–193;

Lele, P. P., 1983, "Physical Aspects and Clinical Studies with Ultrasonic Hyperthermia," Hyperthermia in Cancer Therapy. G. K. Hall and Co., pp. 333–367;

Sleefe, G. E. and Lele, P. P., 1985, "Phased Arrays for the Induction of Local Hyperthermia," Proceedings of the IEEE 1985 Ultrasonics Symposium;

Lele, P. P., 1986, "Rationale, Technique and Clinical Results with Scanned, Focused Ultrasound (SIMFU) System," IEEE Eighth Annual Conference of the Engineering in Medicine and Biology Society;

Lele, P. P., 1987, "Ultrasound: Synergistic Effects and Application in Cancer Therapy by Hyperthermia," Plenum Publishing Corporation;

Lele, P. P., 1987, "Effects of Ultrasound on 'Solid' Mamalian Tissues and Tumors in Vivo," Plenum Publishing Corporation; and Lele, P. P. and J. Goddard, 1987, "Optimizing Insonation Parameters in Therapy Planning for Deep Heating by SIMFU," IEEE Ninth Annual Conference of the Engineering in Medicine and Biology Society.

Further, the following U.S. Patents disclose examples of recent developments in the hyperthermia field:

U.S. Pat. No. 4,441,486 Pounds
U.S. Pat. No. 4,549,533 Cain et al
U.S. Pat. No. 4,586,512 Do-huu et al
U.S. Pat. No. 4,622,972 Giebeler, Jr.

The Pounds patent discloses a hyperthermia system including a plurality of transducers mounted in an isospherical configuration. Each transducer is configured so that its compressional mode of vibration is suppressed near the center.

The Cain et al patent discloses ultrasound generating apparatus having a plurality of side-by-side tapered piezoelectric transducer elements. Means are provided for energizing the transducer elements with electrical energy having a frequency which is varied to modulate the ultrasound produced by the transducer elements.

The Do-huu et al patent discloses an emitter which focuses ultrasonic radiation into biological tissues for producing localized heating. The radiation emitter consists of a piezoelectric plate subdivided into annular radiating zones of equal width by a set of concentric circular grooves.

The Giebeler, Jr. patent discloses an ultrasound hyperthermia applicator comprising a plurality of transducers which can be operated in different grouping modes. The beams from these elements can be individually focused according to a spiral or multi-spiral focusing scheme, in an attempt to provide uniform heating, without scanning, of a volume greater than the inherent focal size of the individual transmitter elements.

Additionally, European Patent Application Ser. No. 214,782 of Umemura et al discloses a transducer composed of a plurality of elements divided at least in a circumferential direction. The phases of drive signals may be changed according to the respective positions of the oscillating elements, to form an annular focal zone having a variable radius.

Certain conventional systems for ultrasonically induced hyperthermia utilize mechanical or electromechanical scanning of the ultrasound transducer, with a scan excursion in the vertical (Z) axis. This Z axis scan excursion necessitates the use of a coupling water bath of a depth approximately equal to the maximum Z axis scan displacement. When insonation is performed in a downward direction, many patients cannot tolerate the great weight of the water bath. Moreover, the electromechanical requirements imposed by scanning the insonation apparatus at appropriate velocities against the force of gravity are difficult and expensive to implement, and present a risk of crush injury to the patient.

Additionally, at the power levels required for ultrasonic hyperthermia, high peak intensities in the focal spots can lead to excessively high temperatures or cavitation, causing unintentional tissue damage. Very high translational speeds are necessary to distribute the energy evenly within the target volume to achieve uniform temperature distributions.

Accordingly, there exists a need for hyperthermia methods and apparatus which allow the focal length and focal direction of the insonation apparatus to be varied without physical Z axis translation of the transducers.

It is accordingly an object of the invention to provide improved ultrasound hyperthermia methods and apparatus.

It is another object of the invention to provide ultrasound hyperthermia methods and apparatus which allow the focal length and focal direction of the insonation transducer to be varied without physical Z axis translation of the transducer.

It is a further object of the invention to Provide ultrasound hyperthermia apparatus which produces uniform heating of the treatment volume.

Other general and specific objects of the invention will in part be obvious and will in part appear hereinafter.

SUMMARY OF THE INVENTION

The foregoing objects are attained by the invention, which provides an ultrasonic hyperthermia system for delivering hyperthermic therapy to a subject. In accordance with one aspect of the invention, the system includes a plurality of piezoelectric transducer elements arranged in an array to provide multiple sources of ultrasonic energy.

The system also includes electrical excitation elements for exciting the transducer elements, including a phase-shifting elements for supplying the transducer elements with electrical excitations having adjustable phases for selectively focusing a beam of ultrasonic energy from the transducer array into a target region of tissue within a subject. The system further includes scanning elements for scanning the focused ultrasonic energy across the target region.

In accordance with another aspect of the invention, the scanning elements are non-linear scanning elements. The non-linear scanning elements can include rotational elements for rotating the focused ultrasonic energy beam to provide the non-linear scanning.

A further aspect of the invention provides an ultrasonic hyperthermia method for delivering hyperthermia therapy to a subject. The method includes arranging a plurality of piezoelectric transducer elements in an array to provide multiple sources of ultrasonic energy, and exciting the transducer elements. The exciting step includes the step of supplying the transducer elements with electrical excitations having adjustable phases for selectively focusing a beam of ultrasonic energy from the transducer array into a target region of tissue within a subject. The exciting step can further include providing adjustable amplitudes for shaping the intensity distribution. This aspect of the invention is referred to as "apodization". The method also includes scanning the focused ultrasonic energy across the target region.

In one embodiment of the invention, the scanning step includes the step of scanning the focused ultrasonic energy in a non-linear pattern. This non-linear scanning can be implemented by rotating the focused ultrasonic energy beam to provide the non-linear scanning.

A further aspect of the invention involves varying the dimensions of the focus region produced by the transducer elements, and the distribution of the energy within that region.

The invention accordingly comprises the steps and apparatus embodying features of construction, combinations of elements and arrangements of parts adapted to effect such steps, as exemplified in the following detailed disclosure, and the scope of the invention is indicated in the claims.

BRIEF DESCRIPTION OF THE DRAWINGS

For a more thorough understanding of the nature and objects of the invention, reference should be made to the following detailed description and the accompanying drawings, in which.

DESCRIPTION OF PREFERRED EMBODIMENTS

Figure 1:
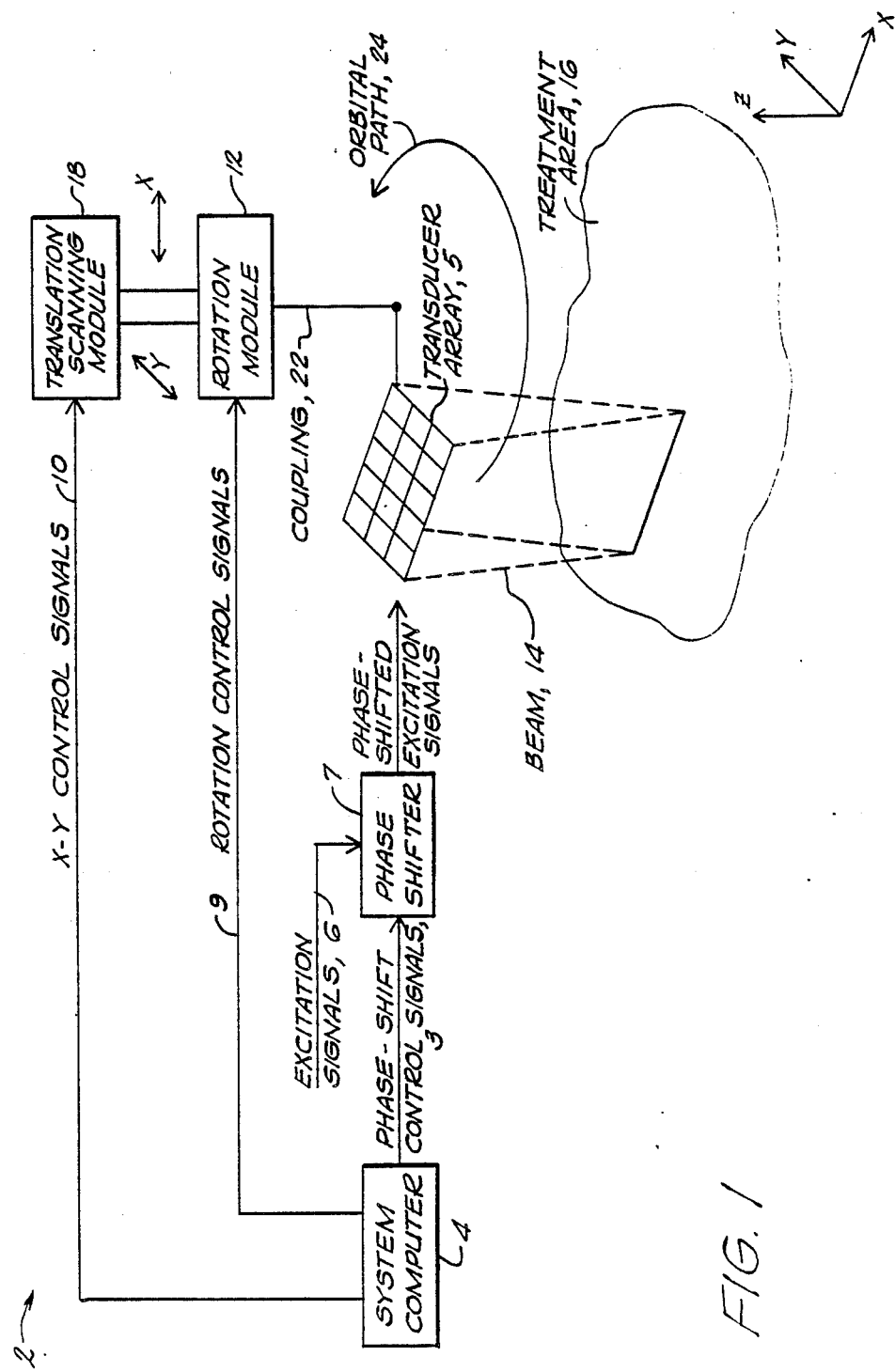
FIG. 1 is a schematic diagram depicting an electronically-controlled variable focus ultrasound hyperthermia system according to the invention.

FIG. 1 depicts an electronically-controlled variable focus ultrasound hyperthermia system according to the invention. The illustrated hyperthermia system 2 includes a system computer 4 and an ultrasound transducer array 5, for generating a beam 14 and directing the beam 14 into treatment area 16. System computer 4 utilized in conjunction with the invention can be any conventional microprocessor, computer, analog circuit, computational device or the like. Those skilled in the art will appreciate that mechanical controls, such as potentiometers, can be substituted for system computer 4.

System computer 4 can generate excitation signals 6 having selected frequency, amplitude and phase. The amplitude of signals 6 can be controlled and varied by system computer 6 to vary the intensity distribution of ultrasound energy. This variation of intensity is referred to as "apodization." Apodization practices are further discussed in commonly owned co-pending U.S. patent applications Ser. Nos. 209,518, 209,519, and 209,520, now U.S. Pat. No. 4,893,624 filed on even date herewith and incorporated herein by reference.

In a preferred embodiment of the invention, excitation signals 6 are transmitted to a phase-shifter 7 controlled by phase-shift control signals 3 generated by system computer 4. Phase-shifter 7 utilizes conventional circuitry for reading phase-shift control signals 3, and shifts the phase of excitation signals 6 to generate phase-shifted excitation signals 1. Phase-shifted amplitude-controlled excitation signals 1 are preferably utilized to provide phase-shift beam steering, in a manner discussed in greater detail below in connection with FIGS. 3A and 3B.

In this preferred embodiment of the invention, phase-shifted excitation signals 1 are transmitted to ultrasound transducer array 5. Ultrasound transducer array 5 is preferably a phased ultrasonic transducer array which produces a line-focus beam 14. In particular, the transducer array can produce a line-focus at a distance which can be dynamically varied by changing the phase delays in the phase-shifted excitation signals 1, as described below in connection with FIGS. 3A and 3B. The transducer array 5 can incorporate a lens for focusing the output of the ultrasound transducer elements.

Referring again to FIG. 1, the transducer array 5 responds to the phase-shifted excitation signals 1 to generate ultrasonic energy. When the invention is practiced in a hyperthermia therapy setting, ultrasound transducer array 5 is connected by coupling 22 to linked translation module 18 and rotation module 12. These position control modules preferably contain stepper motors or servos of conventional design and construction.

As FIG. 1 illustrates, the ultrasound transducer array 5 can be eccentrically mounted to rotation module 12 by means of coupling 22. Rotation module 12, in turn, can be actuated and controlled by angular position signals 9 generated by system computer 4, for rotating ultrasound transducer array 5 through a selected orbital path 24. As a result of this rotation and eccentric placement, the treatment volume 16 is scanned by the beam 14. Moreover, the diameter of the heated field can be more than twice the length of a single line-focus generated by ultrasound transducer array 5, depending upon the radius of gyration of the orbit 24 of ultrasound transducer array 5.

System computer 4 can utilize appropriate software commands to generate translational or rotational patterns to produce prescribed time-averaged intensity distributions in the treatment volume.

Additionally, as shown in FIG. 1, system computer 4 can assert X-Y position control signals 10 to the inputs of translation module 18. Translation module 18 reads the position control signals asserted by system computer 4 and responds by actuating and controlling translational X-Y motion of ultrasound transducer array 5.

Figure 2:
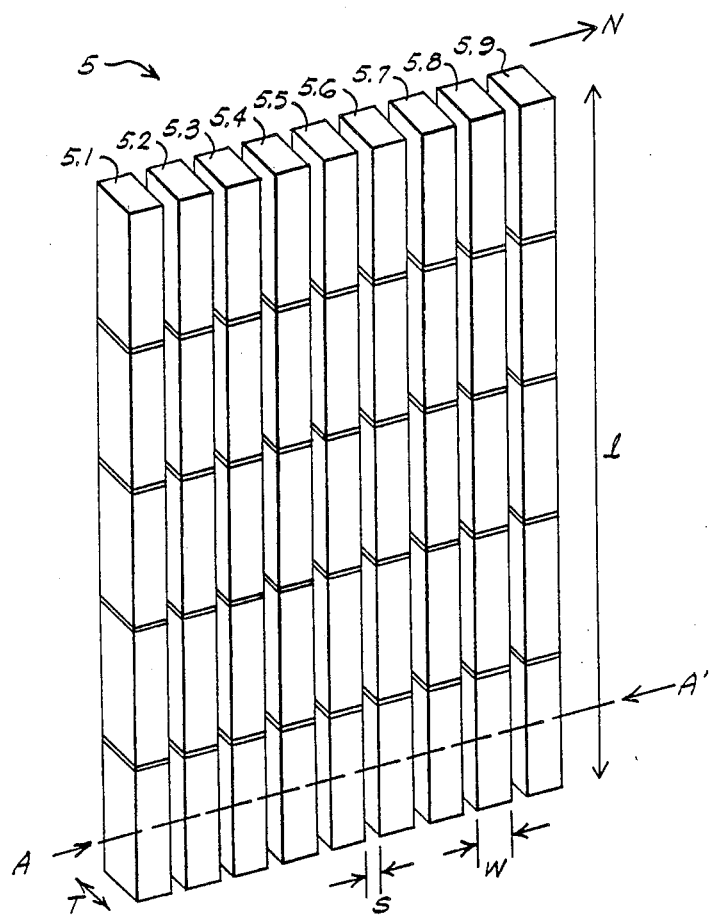
FIG. 2 depicts a transducer array utilized in connection with the system of FIG. 1.

The transducer array 5, shown in FIG. 2, preferably consists of a linear array of N piezoelectric transducer elements 5.1-5.N. Each linear transducer element, in turn, can be composed of five sub-elements, as illustrated in FIG. 2. The excitation phase and amplitude for each sub-element can be individually controlled. The N transducer elements 5.1-5.N can be, for example, 10 to 20 centimeters in length (L). The width (W) of each element, the interelement spacing (S) and thus the number (N) of elements can be optimized as a function of the selected ultrasonic frequency to be generated, in accordance with known engineering principles. The thickness (T) of each element can also be optimized as a function of the selected ultrasonic frequency, depending on the characteristics of the piezoelectric material employed in elements 5.1-5.N. In the embodiment shown in FIG. 2, the thickness T of each transducer element is substantially constant along the length L of each element. The ultrasonic frequency generated by an array 5 in accordance with the invention typically ranges from 500 KHz to 5 Mhz.

Figure 3A:
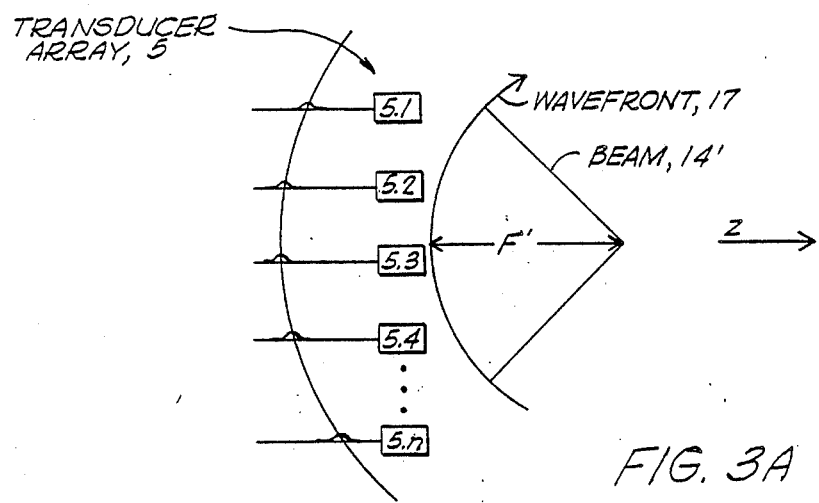
FIGS. 3A and 3B are sectional views of the transducer array of FIGS. 1 and 2, showing ultrasound beams of different focal lengths which can be generated by the system of FIG. 1.
Figure 3B:
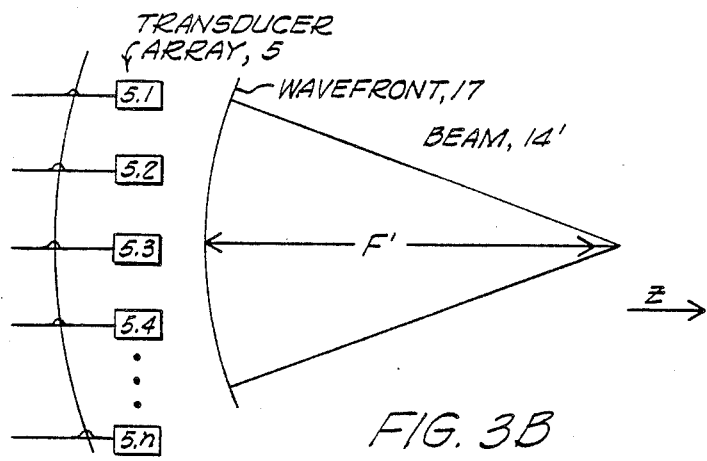

FIGS. 3A and 3B are sectional views taken along line A—A' of the transducer array 5 of FIG. 2, showing ultrasound beams of different focal lengths which can be generated by the transducer array 5. As depicted in FIG. 3A and 3B, the respective focal lengths F, F' of the ultrasound beams 14, 14' can be varied by changing the phase relationships in the sequence of excitation of the individual elements 5.1-5.N, in a manner known in the art.

Figure 4:
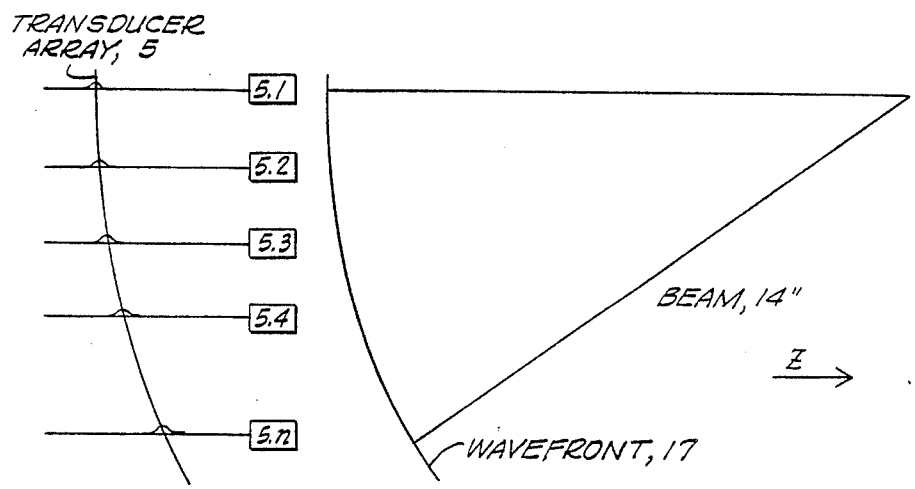
FIG. 4 depicts a beam pattern which can be generated through phase-shift beam steering in the system of FIG. 1.

Additionally, as shown in FIG. 4, the X-Y direction of the beam 14" generated by the array 5 and lens 17 can be changed, without physical translation of the array. In particular, phase-shifter 7 controls the phase of the excitation signals 1 applied to each transducer element 5.1-5.N, to focus and direct the beam, in accordance with beam-steering phenomena known in the art, toward a selected X-Y coordinate in the treatment region 16.

Thus, for example, the focal region of line-focus beam 14 can be varied dynamically by system computer 4 as a function of angular position during rotation, to permit the scanning of irregular target areas.

In a preferred embodiment of the invention, all of the N elements of the array 5 can be activated, or some of the elements can remain unexcited, to vary the effective aperture of the array, and thus the effective depth of field of the array 5. In particular, utilizing a short focal distance, and activating all N elements of the array 5 to produce a large effective aperture, generates a tightly focused ultrasound beam 14. Conversely, activating fewer than all the elements of the array 5, or utilizing a longer focal distance, yields an elongated focal region. Array 5 can thus produce an elongate, substantially linear focal region of selected length.

In another embodiment of the invention, the length of the line-focus 14 can also be changed for a given treatment area 16 by placing ultrasound absorbing material at selected regions between the array and the treatment area. Such materials, well known in the art, can be positioned so as to block selected portions—typically the outermost extent—of the line focus beam 14, thereby truncating the beam 14.

Those skilled in the art will appreciate that a significant advantage of the invention lies in its ability to electronically vary the focal depth of the beam 14 generated by the transducer array 5. This variable focal depth feature of the invention eliminates the requirement of Z axis translation of the transducer array 5 during hyperthermia treatment. Instead, as depicted in FIG. 1, the transducer array 5 can be scanned across the treatment area 16 utilizing only rotational module 12 and X-Y translation module 18. Translation in the Z axis can be implemented, if desired, for selected initial positioning of the transducer array 5.

Sweeping the beam 14 through a selected orbital path 24 as depicted in FIG. 1, in combination with dynamic focusing adjustments, produces uniform heating of the target volume at all depths. Uniformity is enhanced by utilizing apodization in connection with a raster scan pattern to equalize time-averaged energy deposition throughout the target volume.

Moreover, in a further aspect of the invention, complex heating patterns can be generated by combining X and Y axis translational motions, actuated and controlled by translation module 18, with the rotation generated by rotation module 12.

Further embodiments can provide spiralling heating patterns, zig-zag heating patterns and the like to also induce uniform heating throughout a target volume while avoiding excessive heating in any one region.

It will thus be seen that the invention efficiently attains the objects set forth above, among those made apparent from the preceding description. In particular, the invention provides an electronically-controlled variable focus ultrasonic hyperthermia system which provides a variable-depth beam capable of heating both deep and irregularly shaped tumors, and which delivers enhanced levels of total power while eliminating high peak intensities. The invention also reduces the requirement of vertical (Z axis) motion which would require movement of the transducer into dangerous proximity with the patient.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

Having described the invention, what is claimed as new and secured by Letters Patent is:

1. An ultrasonic hyperthermia system for delivering hyperthermia therapy to a subject, the system comprising:
   ultrasonic transducer means, including a plurality of piezoelectric transducer elements, said transducer elements having a substantially constant thickness, said transducer elements being arranged in an array to provide multiple sources of ultrasonic energy, for generating a beam of ultrasonic energy characterized by an elongate, substantially linear focal region or selected length at a selected depth in the subject;
   an electrical excitation means for exciting said transducer elements, said electrical excitation means including electronic control means for dynamically and electronically varying the length and depth of the substantially linear focal region, said electronic control means including a phase-shifting means for supplying the transducer elements with electrical excitations having adjustable phases for dynamically varying the length and depth of the substantially linear focal region to selectively focus the beam of ultrasonic energy from the transducer array into a target region of treatment area within the subject; and scanning means for scanning the focused ultrasonic energy across said target region.

2. The system of claim 1 further comprising means for supplying the transducer elements with electrical excitations having selected amplitudes.

3. An ultrasonic hyperthermia system for delivering hyperthermia therapy to a subject, the system comprising:

ultrasonic transducer means, including a plurality of piezoelectric transducer elements arranged in an array to provide multiple sources of ultrasonic energy, for generating a beam of ultrasonic energy characterized by a substantially linear focal region of selected length at a selected depth in the subject;

an electrical excitation means for exciting said transducer elements, said electrical excitation means including electronic control means for dynamically and electronically varying the length and depth of the substantially linear focal region, said electronic control means including a phase-shifting means for supplying the transducer elements with electrical excitations having adjustable phases for dynamically varying the length and depth of the substantially linear focal region to selectively focus the beam of ultrasonic energy from the transducer array into a target region of treatment area within the subject; and scanning means for scanning the focused ultrasonic energy across said target region, the scanning means including means for scanning the focused ultrasonic energy across said target region in a non-linear pattern.

4. The system of claim 3 wherein the means for scanning the focused ultrasonic energy in a non-linear pattern includes a rotational means for rotating the focused ultrasonic energy beam to provide the scanning in a non-linear pattern.

5. An ultrasonic hyperthermia method for delivering hyperthermia therapy to a subject, the method comprising the steps of:

arranging a plurality of piezoelectric transducer elements having a substantially constant thickness in an array to provide multiple sources of ultrasonic energy;

exciting said transducer elements to generate a beam of ultrasonic energy characterized by an elongate, substantially linear focal region of selected length at a selected depth in the subject, said exciting step including the step of supplying the transducer elements with electrical excitations having adjustable phases for dynamically and electronically varying the length and depth of the substantially linear focal region, to selectively focus the beam of ultrasonic energy from the transducer array into a target region of treatment area within a subject; and scanning the focused ultrasonic energy across the target region.

6. The method of claim 5 wherein the exciting step includes the step of supplying the transducer elements with electrical excitations having selected amplitudes.

7. An ultrasonic hyperthermia method for delivering hyperthermia therapy to a subject, the method comprising the steps of:

arranging a plurality of piezoelectric transducer elements in an array to provide multiple sources of ultrasonic energy;

exciting said transducer elements to generate a beam of ultrasonic energy characterized by a substantially linear focal region of selected length at a selected depth in the subject, said exciting step including the step of supplying the transducer elements with electrical excitations having adjustable phases for dynamically and electronically varying the length and depth of the substantially linear focal region, to selectively focus the beam of ultrasonic energy from the transducer array into a target region of treatment area within a subject; and scanning the focused ultrasonic energy across said target region, the scanning step including the step of scanning the focused ultrasonic energy in a non-linear pattern.

8. The method of claim 7 wherein the non-linear scanning step includes the step of rotating the focused ultrasonic energy beam to provide the non-linear scanning.

* * * * *